US007706858B1

(12) United States Patent
Green et al.

(10) Patent No.: US 7,706,858 B1
(45) Date of Patent: Apr. 27, 2010

(54) HEAD AND NECK IMMOBILIZATION IN MAGNETIC RESONANCE IMAGING

(75) Inventors: Charles A. Green, Holbrook, NY (US); Jan Votruba, Ridge, NY (US); William H. Wahl, Smithtown, NY (US); Arto Cinoglu, Mellville, NY (US)

(73) Assignee: Fonar Corporation, Melville, NY (US)

( * ) Notice: Subject to any disclaimer, the term of this patent is extended or adjusted under 35 U.S.C. 154(b) by 383 days.

(21) Appl. No.: 10/434,959

(22) Filed: May 9, 2003

(51) Int. Cl.
*A61B 5/05* (2006.01)

(52) U.S. Cl. .................. 600/415; 600/407; 600/410; 600/417; 600/421; 600/422; 5/601; 5/622; 128/97.1; 606/130

(58) Field of Classification Search .............. 5/662, 5/601; 600/415, 417; 606/130; 128/97.1
See application file for complete search history.

(56) References Cited

U.S. PATENT DOCUMENTS

| | | | |
|---|---|---|---|
| 5,062,415 A | 11/1991 | Weatherby et al. | |
| 5,081,665 A * | 1/1992 | Kostich | 5/637 |
| 5,171,296 A | 12/1992 | Herman | |
| 5,197,474 A | 3/1993 | Englund et al. | |
| 5,349,956 A | 9/1994 | Bonutti | |
| 5,566,681 A | 10/1996 | Manwaring et al. | |
| 5,640,958 A | 6/1997 | Bonutti | |
| 5,680,861 A * | 10/1997 | Rohling | 600/407 |
| 5,743,264 A | 4/1998 | Bonutti | |
| 5,836,878 A | 11/1998 | Mock et al. | |
| 5,855,582 A * | 1/1999 | Gildenberg | 606/130 |
| 5,947,981 A | 9/1999 | Cosman | |
| 5,988,173 A | 11/1999 | Scruggs | |
| 6,122,541 A | 9/2000 | Cosman et al. | |
| 6,138,302 A | 10/2000 | Sashin et al. | |
| 6,141,579 A | 10/2000 | Bonutti | |
| 6,198,961 B1 * | 3/2001 | Stern et al. | 600/422 |
| 6,246,900 B1 | 6/2001 | Cosman et al. | |
| 6,357,066 B1 | 3/2002 | Pierce | |
| 6,404,202 B1 * | 6/2002 | Damadian et al. | 324/318 |
| 6,414,490 B1 | 7/2002 | Damadian et al. | |
| 2002/0032927 A1 | 3/2002 | Dinkler | |

OTHER PUBLICATIONS

RSNA photograph of around 2000.
U.S. Appl. No. 08/978,084, filed Nov. 25, 1997.
U.S. Appl. No. 09/718,946, filed Nov. 22, 2000.
U.S. Appl. No. 10/131,843, filed Apr. 25, 2002.

* cited by examiner

*Primary Examiner*—Brian Casler
*Assistant Examiner*—James Kish
(74) *Attorney, Agent, or Firm*—Lerner, David, Littenberg, Krumholz & Mentlik, LLP

(57) ABSTRACT

Apparatus, system and method for immobilizing a patient's head during imaging. The apparatus includes two substantially C-shaped members that are pivotably mounted to each other. One C-shaped member includes at least one adjustable positioning rod for securing the patient's head during imaging. The apparatus is attached to a magnet resonance imaging apparatus to form a system. The system is used for imaging a patient whose head and neck is immobilized by the apparatus.

19 Claims, 10 Drawing Sheets

HEAD AND NECK IMMOBILIZATION IN MAGNETIC RESONANCE IMAGING

BACKGROUND OF THE INVENTION

The present invention relates to magnetic resonance imaging systems, apparatus and procedures. In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing automatic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Several factors affect the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the long axis or head-to-toe axis of the patient's body must be in a horizontal position during the procedure. Moreover, equipment of this type provides a claustrophobic environment for the patient.

Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal. This affects the conditions under which imaging may be performed and also affects the comfort level of the patient.

Recently, magnets having horizontal pole axes that provide an open patient environment have been developed. As disclosed, for example, in commonly assigned U.S. Pat. No. 6,414,490 (the "'490 patent"), which is a continuation of U.S. patent application Ser. No. 08/978,084, filed on Nov. 25, 1997, and in co-pending, commonly assigned U.S. patent application Ser. No. 09/718,946 (the "'946 application"), filed on Nov. 22, 2000, the disclosures of which are incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the aforesaid applications, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

The position of a patient during magnetic resonance imaging may affect or limit the imaging information obtained. A patient may exhibit a symptom if oriented in an upright or weight bearing position and no symptom if oriented in a recumbent or horizontal position. For example, it may be necessary to image a patient in an upright or gravity bearing position to discern a symptom and provide a diagnosis for injuries relating to the neck, spine, hip, knee, foot or ankle areas of the human anatomy.

In addition to a patient's position, movement by a patient during imaging may also affect the images obtained. In fact, magnetic resonance imaging procedures generally require the patient to remain perfectly still during imaging. A patient positioned in a weight-bearing upright posture may find it more difficult to remain still during imaging. The anxiety level of a patient is another factor that may affect how still a patient remains during imaging. In general, those magnets that place the patient in the bore of the magnet during imaging tend to add to the patient's anxiety level because of the closed-in and tight environs. A more relaxed patient tends to move less during imaging.

It is often desirable to provide fixtures in close proximity to the patient. For example, local antennas such as small solenoidal coils can be placed around a part of the patient's body to be imaged as, for example, around the head or around a limb of the patient. These antennas can be used to transmit the RF excitation signals, to receive the magnetic resonance signals emitted by the tissue, or both. Such local antennas allow improved reception of signals from the specific region of interest within the patient's body. Other fixtures can be used for purposes such as supporting or positioning parts of the patient's body relative to the table as, for example, a rest for supporting the patient's head or limb. Typically, these fixtures are simply placed on the surface of the bed at the desired location for a particular patient, or are placed on the patient's body so that the fixture will be supported by the bed surface when the patient lies on the bed surface. These arrangements are satisfactory where the bed remains in a horizontal position at all times.

Where the patient support table is in a generally vertical orientation during all or a portion of the procedure, fixtures positioned on the surface of the support will fall off of the support unless they are secured to the surface. Although the fixtures can be secured to the support using devices improvised for a particular application, as, for example, straps or tape, such arrangements do not offer a complete solution. Accordingly, there has been a need for improved apparatus for positioning fixtures in magnetic resonance apparatus, and for magnetic resonance apparatus incorporating such improved positioning apparatus. In particular, there is a need for fixtures that can immobilize a patient's head and neck in a variety of orientations without adding to a patient's anxiety.

SUMMARY OF THE INVENTION

An aspect of the present invention is a device for immobilizing a patient's head and/or neck. The device comprises two substantially C-shaped members that are pivotably connected to each other. The first C-shaped member includes at least one positioning member that is used to secure the patient's head.

In an embodiment, the first C-shaped member includes an inner surface, an outer surface, first and second fastener apertures and at least one aperture for insertion of the at least one positioning member. The second C-shaped member includes an inner surface and an outer surface and first and second fastener apertures. The first and second C-shaped members are secured at each of the first and second apertures to form a halo into which a human head may be inserted.

In accordance with another aspect of the present invention, the at least one aperture further includes a flexible magnetically translucent retainer that engages the positioning member such that the positioning member is fixed.

Further in accordance with this embodiment, the at least one positioning member comprises a rod member having a flattened portion that terminates a substantially circular portion. When the flattened portion of the rod member is adjacent to the retainer the rod is free to move and when the rod member circular portion is adjacent the retainer the rod is held in place.

Another aspect of the present invention is a system for magnetic resonance imaging comprising a magnet defining a patient-receiving space and having a static magnetic field with a field vector in a substantially horizontal direction. The magnet further includes a patient support disposed within said patient-receiving space. The patient support is fitted with a head and immobilization device. A patient is then positioned on the patient support such that the patient's head is secured to the patient support. Magnet resonance imaging of the patient then proceeds.

Another aspect of the present invention is a method for magnetic resonance imaging comprising positioning a patient on a patient support in a space between a pair of opposed pole faces separated apart from one another along a horizontal pole axis such that the head of the patient is located within a head immobilization halo. A substantially horizontal static magnetic field is then established between the pole faces and magnetic resonance signals are elicited by transmitting radio frequency (RF) energy to the body of the patient and receiving the magnetic resonance signals.

Further in accordance with the method positioning may include positioning the patient in a substantially upright position or a substantially horizontal position or any position between substantially upright and horizontal. In addition, the patient may also be positioned in a sitting position.

DETAILED DESCRIPTION

Figure 1A:
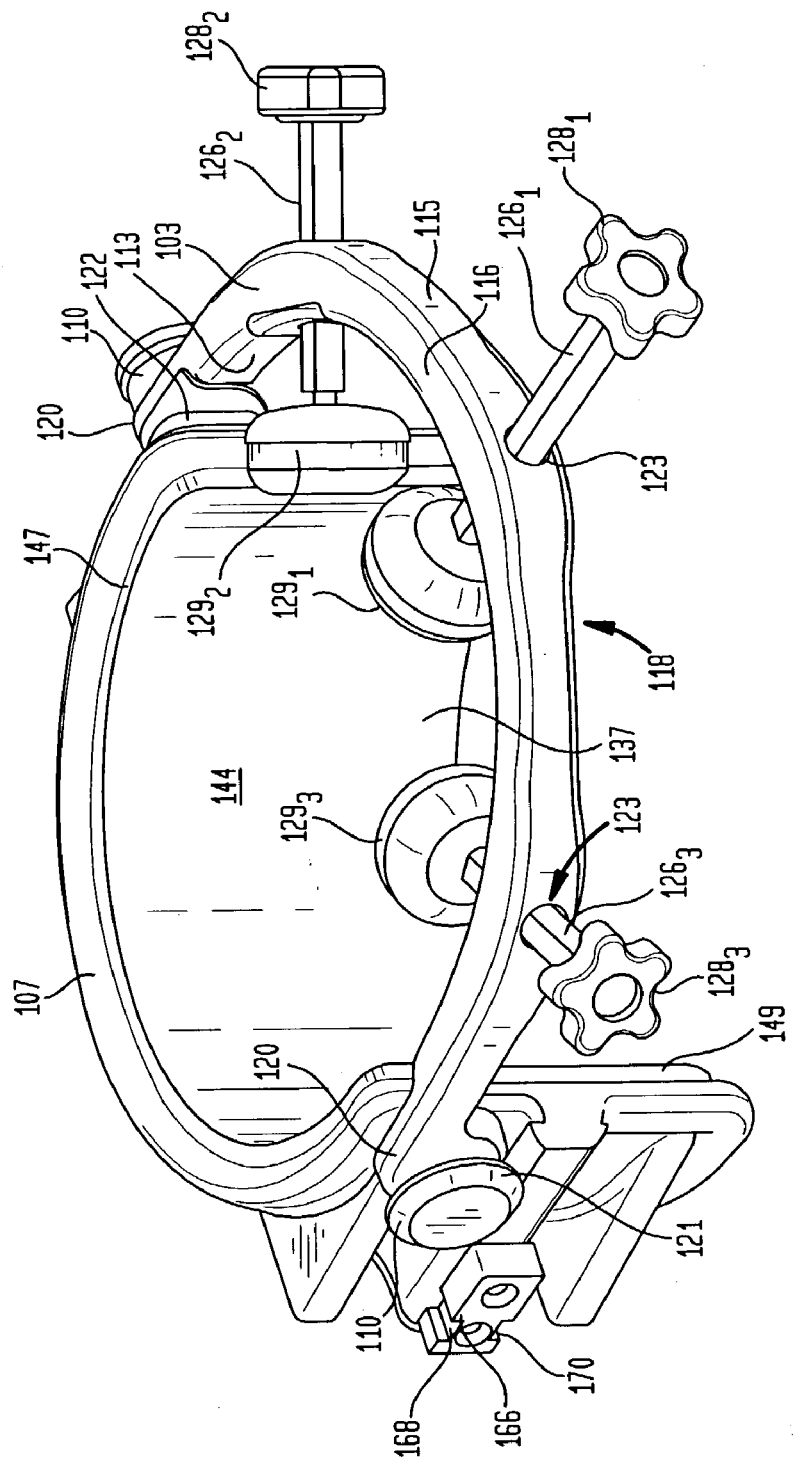
FIG. 1A illustrates a perspective view of a head and neck immobilization device in accordance with an aspect the present invention.
Figure 1B:
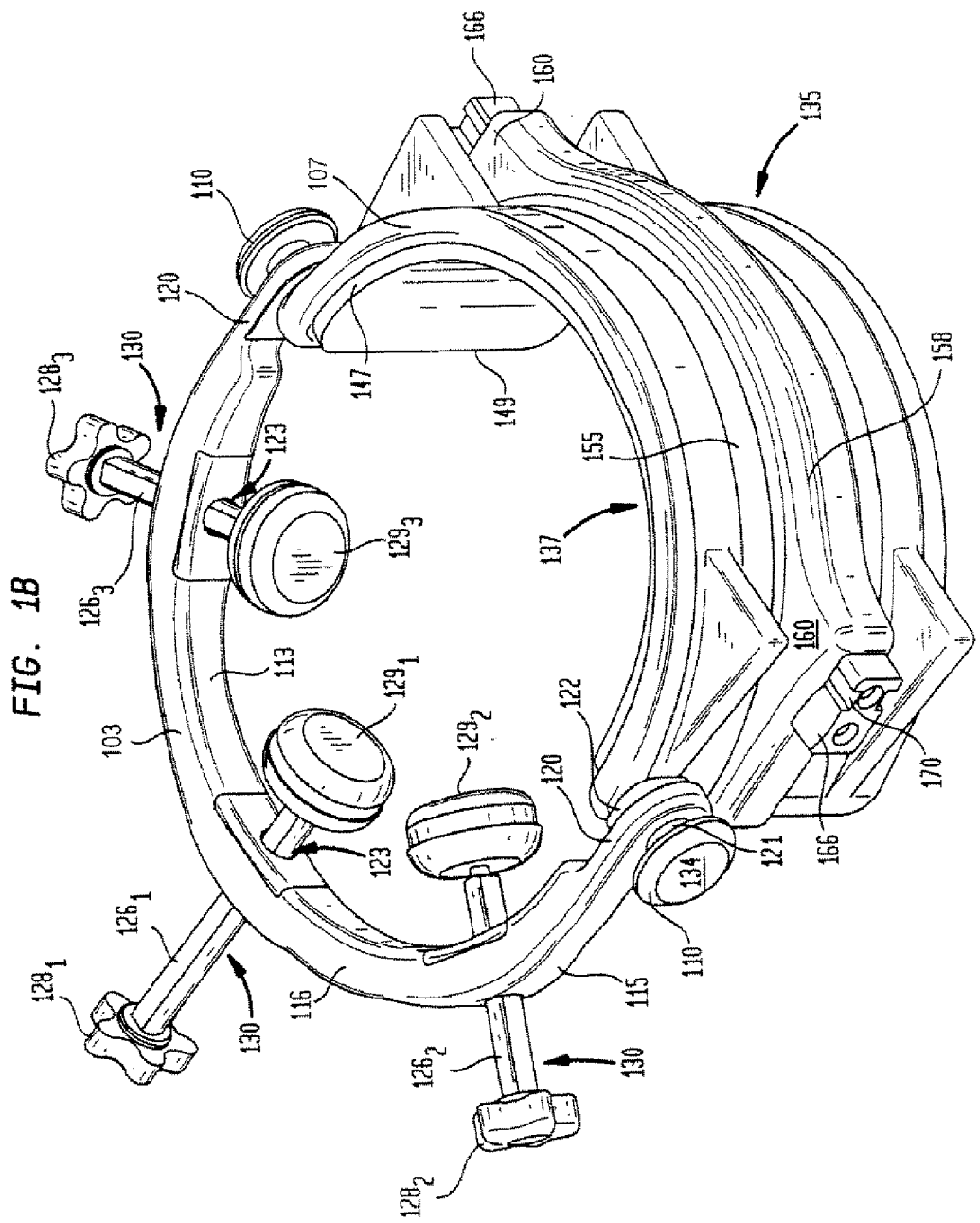
FIG. 1B illustrates another perspective view of the device of FIG. 1A.

An aspect of the present invention is a head and neck immobilization device or halo 100 as shown in FIG. 1, in which FIG. 1A and FIG. 1B show front and rear perspective views of the device 100, respectively. The device 100 comprises a first substantially C-shaped or arcuate member 103 and a second C-shaped or arcuate member 107. The first and second C-shaped members 103 and 107 are mounted to each other by pivot mechanism 110. Pivot mechanism 110 advantageously allow first C-shaped member 103 to pivot about second C-shaped member 107 or vice-versa.

The first C-shaped member 103 includes an inner side wall 113 and an outer side wall 115. The inner side wall 113 defines an inner surface. The outer side wall 115 similarly defines an outer surface. The inner and outer side walls 113, 115 are terminated at an end by upper lateral wall 116 and at another end by lower lateral wall 118. In a preferred embodiment, the edges at the intersection of side walls 113, 115 and lateral walls 116, 118 are rounded or smoothed to protect against injury, e.g., cuts, during handling.

The first C-shaped member is terminated at each end by donut-shaped pivot points 120, which each include fastening or pivot aperture 121 formed through the inner and outer side walls 113 and 115. In a preferred embodiment, the width of the lateral side walls 116, 118 become narrower or slope at the pivot points 120 to allow for insertion of optional washer 122 during assembly. The washer 122 functions to relieve tension between the C-shaped members yet while ensuring tightness of the entire assembly.

The first C-shaped member further includes one or more apertures 123 into which are inserted one or more positioning rods 126. Apertures 123 allow the positioning rods 126 to be slideably mounted into first C-shaped member 103 so as to hold a patient's head in place. Although in a preferred embodiment the positioning rods 126 are slidably mounted, it is possible to mount the rods 126 so that their position is adjusting by a screwing or rotating motion. In addition, in a preferred embodiment three positioning rods $126_1$, $126_2$, $126_3$ are used. However, it is possible to use only center rod $126_1$, or the two off-center rods $126_2$ and $126_3$ to hold a patient's head stationary.

Each positioning rod 126 includes a handle or knob 128 and a patient contact portion 129. The knob 128 and contact portion 129 are mounted to each end of a rod 130. The knob 128 is used by a technician or other personnel to adjust the position of the contact position 129 relative to the head of a patient. The knob 128 lends itself to any design that may be conveniently maneuvered by the technician's hand. The contact portion 129 preferably comprises a rubbery, soft plastic, or other form of rubbery material that provides a non-abrasive cushiony contact surface for a patient's head. As shown, the contact surface of the contact portion 129 is preferably circular, although other shapes may be used.

As previously discussed, the first C-shaped member 103 includes pivot apertures 121. The pivot apertures 121 are engineered to receive a pivot member 110. The pivot member 110 includes a knob 134 and a rod which is inserted through pivot apertures 121 into a pivot opening (not shown) on second C-shaped member 107. Together the pivot member 110 along with the apertures 121 and the pivot opening on the second C-shaped member form a pivot mechanism. The pivot mechanism is arranged such that the adjustment of the knob 134 allows the first C-shaped member to be flipped up above the head of a patient. This allows the patient to place his or her head into and out of the device 100 before and after imaging. During imaging, the first C-shaped member is flipped down and held in place by tightening knob 134. The pivot member 110 may be keyed at its end opposite the knob 134. The pivot member may also be threaded at its end opposite the knob 134 so that rotation in one direction engages threading in the pivot opening on the second C-shaped member so as to tighten the pivot mechanism. Rotation in the opposite direction would then loosen the pivot mechanism allowing the first C-shaped portion 103 to pivot about the second C-shaped portion 107.

In the embodiment shown in FIG. 1, the pivot mechanism is arranged with the first C-shaped member 103 being connected to the second C-shaped member such that a portion of the inner side wall 113 of first member 103 is adjacent to a portion of the outer side wall 135 of the second C-shaped member 107. In an alternative of the embodiment the pivot mechanism may be arranged such that a portion of the outer side wall 115 of first member 103 is adjacent to a portion of the inner side wall 137 of the second member 107 at the pivot openings.

As noted above, the second C-shaped member includes an inner side wall 137 and an outer side wall 135. The inner side wall 137 defines an inner support surface which, in a preferred embodiment, comprises a pad 144 having a substantially arcuate lengthwise side wall 147. The pad 144 may be made of foam or other similar material. The side walls 147 terminate on substantially traverse longitudinal side walls 149.

In the embodiment shown, each of the side walls, 147 and 149, are of substantially the same thickness. It is also possible to make a pad 144 wherein the side walls 147 are thicker at their outer edges than at their center thereby allowing the longitudinal side wall 149 to have a wider width, which allows for a structure which further enhances immobilization of the neck and head. In a preferred embodiment side walls 147 and 149 are approximately 1.27 centimeters or 0.5 inch.

The pad 144 advantageously defines an area against which the back of a patient's head may be supported, which, in turn provides a support surface for the device 100. As shown, the pad 144 is adhesively mounted to the inner surface of a base member 155 that forms second C-shaped member 107. In addition to adhesive mounting, the pad 144 may be fastened to the base 155 using any number of fasteners, including screws, rivets, pins, studs, etc.

The outer surface of the base 155 defines the outer surface 135 of the second member 107. In the particular embodiment shown, the outer surface 135 of the base 155 includes an arcuate rib member 158. The rib member 158 includes a pair of flanges 160, which include a first and second rectangular blocks 166 projecting from a side wall surface of the flanges 160. The blocks 166 are mountable into a universal receiving unit as is described in commonly assigned U.S. patent application Ser. No. 10/131,843, filed on Apr. 25, 2003 (the '843 application), the disclosure of which is incorporated in its entirety by reference herein.

Figure 2:
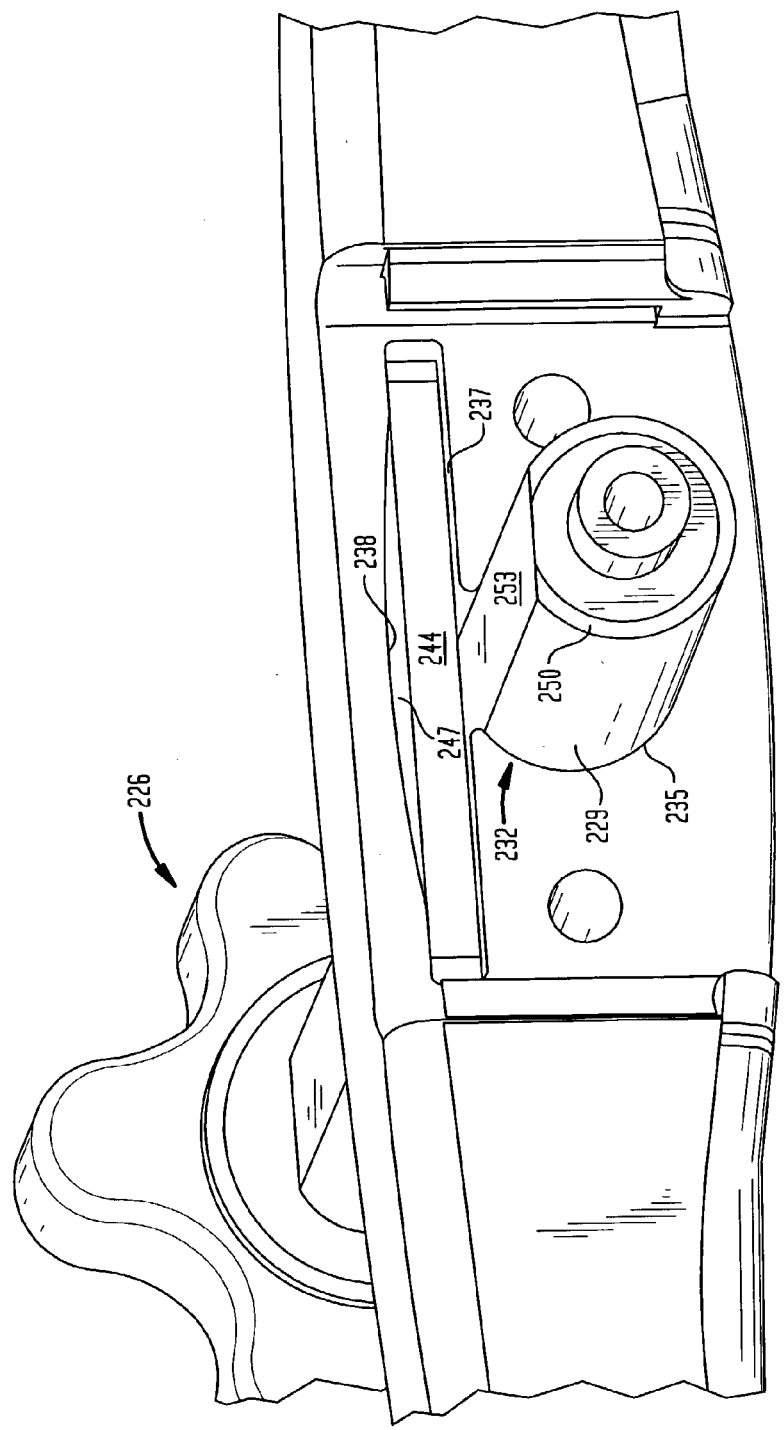
FIG. 2 is an exploded view of a positioning rod with the patient contact portion removed in accordance with an aspect of the present invention.

Turning now to FIG. 2, there is shown an exploded view of a positioning rod locking mechanism with the patient contact portion 129 removed in accordance with an additional aspect of the present invention. As shown, the positioning rod 226 includes a rod member 229 that is inserted through an aperture 232 formed through the inner and outer side walls 113, 115 of first C-shaped member 103. In the embodiment shown, the aperture 232 includes a substantially circular opening 235 and a substantially rectangular opening 237 having an arcuate edge 238. The substantially rectangular opening 237 and circular opening 235 together form the positioning rod opening in accordance with this embodiment.

A substantially rectangular retainer 244 is mounted into rectangular opening 237 thereby leaving an air gap 247 when the positioning rod is in an adjustable position. The retainer 244 may be made from a flexible piece of G-10 polymer, nylon, Delrin, PBC or virtually any plastic material. Such materials should provide mechanical stability, be light and magnetically transparent. The rod member 229 includes a circular run or surface 250 that terminates at a flattened top position 253. In the adjustable position the flattened position 253 is positioned adjacent to the retainer 244 or rectangular opening 237. In this position, the positioning rod 226 may slide in a direction substantially transverse to the plane defined by the side walls 113 and 115 and thereby be adjusted to fit the head of the patient.

To lock the rod 226 into place, the rod 226 is rotated such that the circular position 235 abuts the retainer 244. The retainer 244 then flexes to occupy air gap 247 and abuts the arcuate edge 238. In accordance with this novel design, the rod is fixed into place by a simple turning motion. This advantageously allows the rod to be fixed and remain in place without a screwing type motion. This lengthens the life of the device 100 avoiding thread wear common in magnetically translucent fasteners, e.g., plastic screws or locking devices.

Figure 3A:
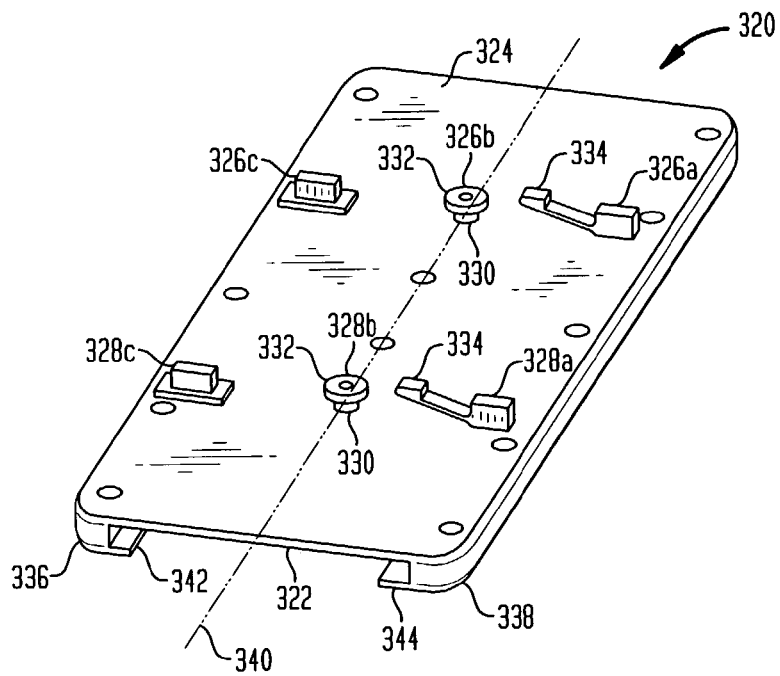
FIGS. 3A and 3B depict perspective views of a component of fixture positioning apparatus in accordance with an embodiment of the present invention.

Turning to FIG. 3, there is shown a positioning apparatus in accordance with an embodiment of the invention, including a universal mounting unit 320. As previously stated, the mounting unit along with other structure are described in the '843 application, the disclosure of which is incorporated by reference herein. The mounting unit includes a lower plate 322 having a bottom surface 324. A first set of guide elements 326a-326c projects from the bottom surface in a row extending across the bottom plate. A second set of guide elements 328a-328c also projects from the bottom surface. The guide elements of the second set are arranged in a row parallel to the row formed by the first set of guide elements 326. The first set of guide elements includes a center guide element 326b in the form of a shoulder bolt having a relatively small diameter neck portion 330 adjacent the bottom face 324 of the bottom plate and having a relatively large diameter head 332 spaced away from the bottom face 324. The remaining guide units 326a and 326c of the first set are generally rectangular, solid elements. The guide elements 328 of the second set include end elements 328a and 328c, similar to the end elements 326a and 326c of the first set, and a center guide element 328b, similar to those of center guide element 326b. A pair of resilient arresting elements 334 is formed integrally with the end guide elements 326a and 328a. These end elements are flexible in directions towards and away from the bottom plate 322, i.e., upwardly and downwardly as seen in FIG. 3A.

Figure 3B:
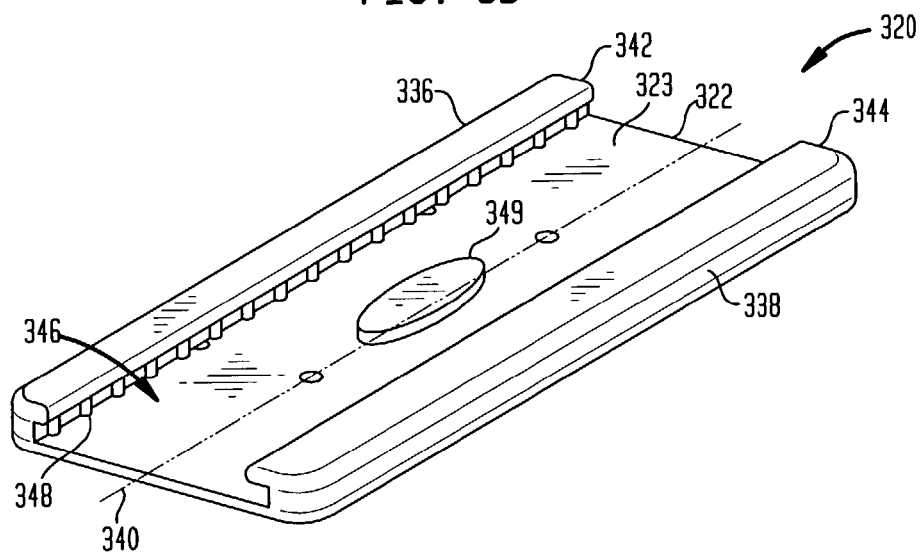

As depicted in FIG. 3B, mounting unit 320 is inverted relative to the position shown in FIG. 3A, so that the top surface 323 of the bottom plate 322 is facing upwardly in FIG. 3B. The mounting unit has a pair of side rails 336 and 338 projecting upwardly from the top surface 323. The side rails extend generally in a track direction, i.e., the direction indicated by axis 340. Rails 336 and 338 (FIG. 3B) extend generally along opposite edges of bottom plate 322. The first rail 336 has a flange 342 projecting inwardly from the upper end of the rail, i.e., the edge of the rail remote from bottom plate 322. The second rail 338 has a similar flange 344 projecting inwardly towards rail 336. The rails, flanges and bottom plate 322 cooperatively define a track in the form of a generally T-shaped slot 346 extending in track direction 340. The first rail 336 is provided with a series of detent bumps 348 disposed between flange 342 and bottom plate 322. Detent bumps 348 are disposed at regular intervals as, for example, about 2.5 cm (one inch) between detent bumps. A stop 349 projects upwardly from the top surface 323 of bottom plate 322 within slot 346. As seen in FIG. 3A, the first rows of guide elements 326 extend transverse to the track direction 340 and the second row of guide elements 328 also extends transverse to the track direction.

A universal fixture-receiving unit 350 (FIGS. 4A and 4B) includes a base plate 352 having a pair of oppositely directed long edges 354 and 356 and an elongated central slot 358. A pair of end risers or units 360 and 362 project upwardly from the base plate 352 at opposite ends thereof. End riser 362 has a generally rectangular slot 364 in its inner face, the face of riser 362 facing toward the opposite riser 360. Slot 364 is open to the upper end of riser 362 facing away from base plate 352.

A latch 366 projects into slot 364. The latch has a gradually sloping face facing toward the open end of slot 364. Latch 366 is carried on a resilient spring arm 368, seen in broken lines in FIG. 4A, disposed within a cavity in end unit 364. The cavity is covered by a plate 370. A release button 372 is exposed at an edge of end unit 362. Button 372 is connected through a rod 374 to spring arm 368, so that when button 372 is depressed manually, latch 366 is moved out of slot 364. The opposite end unit 360 has a slot 376 equipped with a similar latch 377, resilient arm 379, and a similar release button 378.

A pair of plates 380 and 382 projects upwardly from the base plate 352 and extend between end risers 360 and 362. Plates 380 and 382 are spaced inwardly from edges 354 and 356 of the base plate 352. Thus, a region of the base plate between first edge 354 and plate 380 defines a first lip 384, whereas another portion of the base plate between plate 382 and second edge 356 defines another lip 386. Plates 380 and 382 have semicircular indentations 388 and 390 in their top edges so that these plates cooperatively define a cradle in the form of a sector of a circular cylinder having a cradle axis 392. The cradle axis extends transverse to the edges 354 and 356 of the base plate and, hence, transverse to the direction of elongation of the base plate.

Figure 4A:
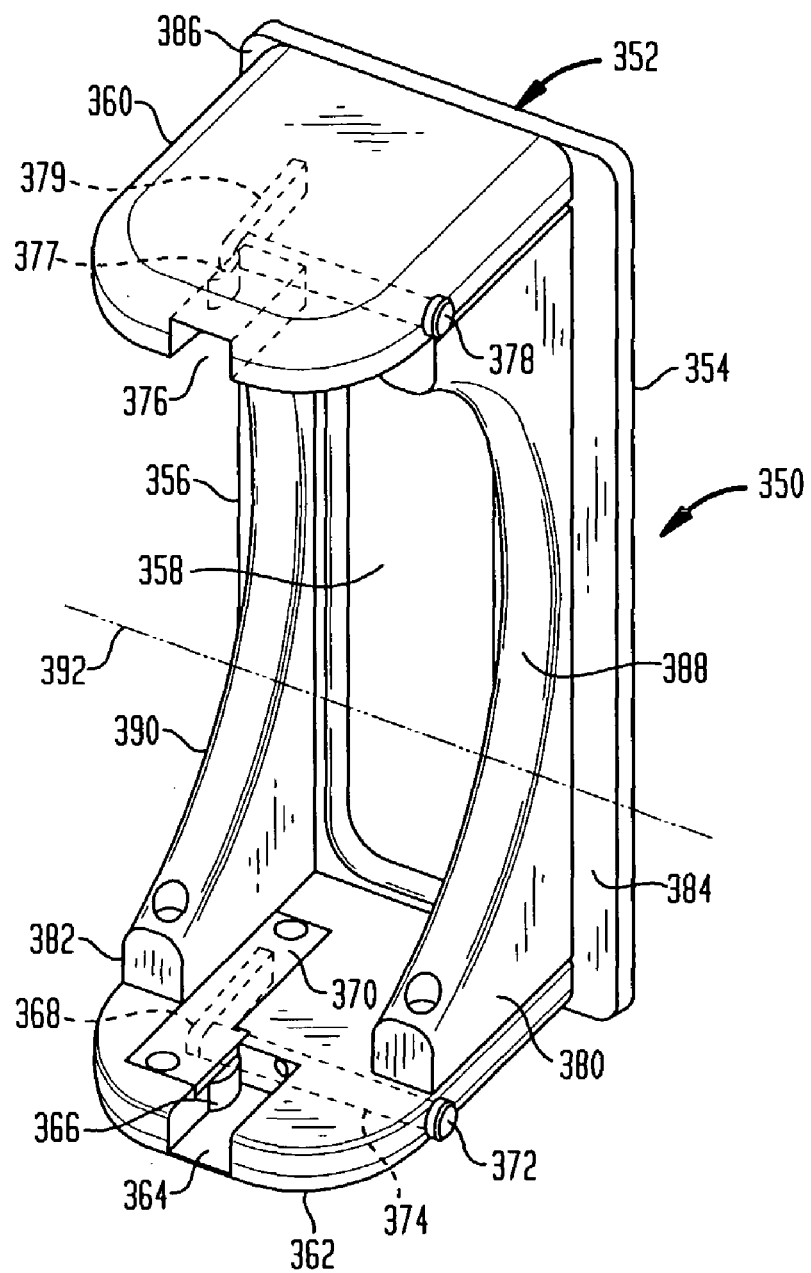
FIGS. 4A and 4B depict perspective views of another component, a universal fixture receiving unit, usable with the component of FIG. 3.
Figure 4B:
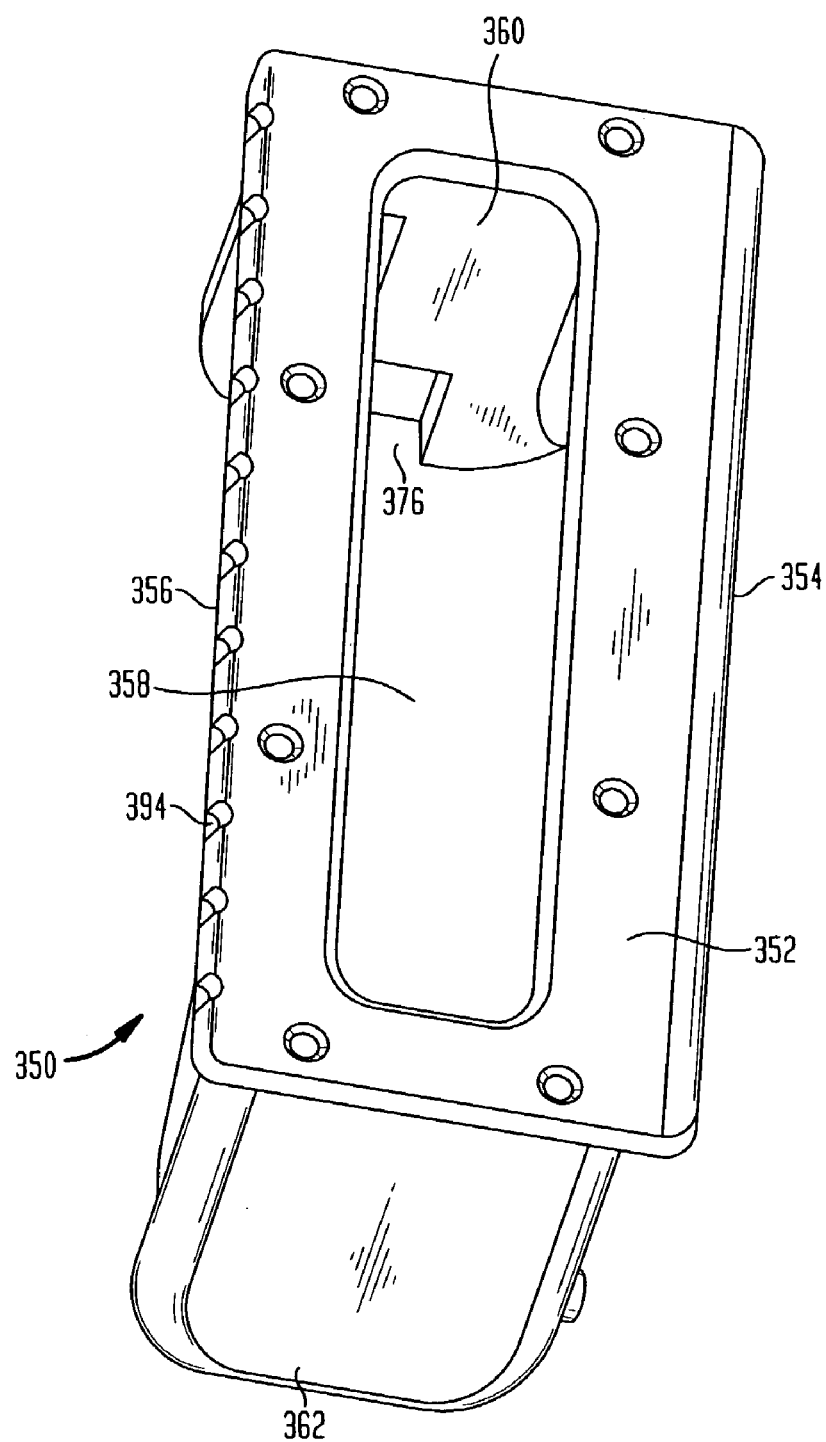

As best seen in FIG. 4B, the second edge 356 of base plate 354 is provided with a series of detent notches 394 spaced apart from one another at regular intervals along the length of the edge. The spacings between notches 394 correspond to the spacings between detent bumps 348 of the mounting unit (FIG. 3B).

Figure 5:
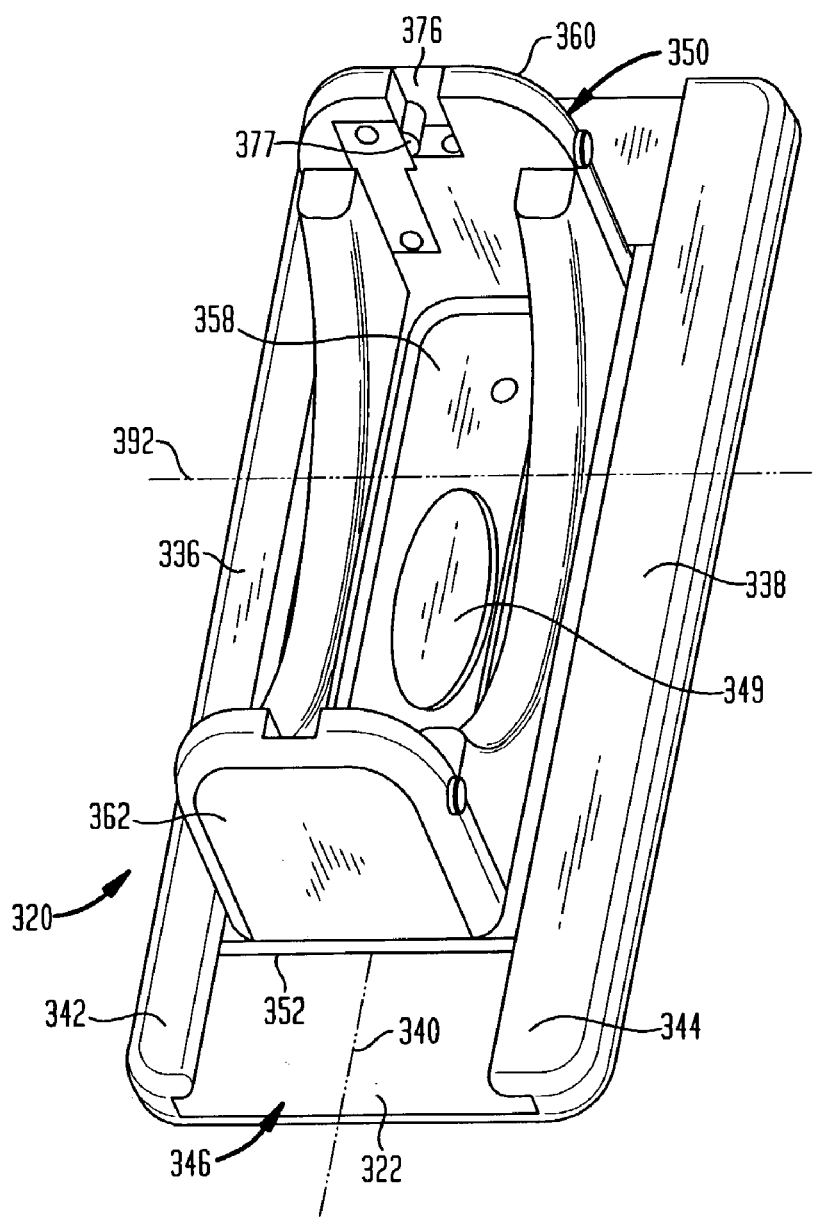
FIG. 5 is a diagrammatic perspective view of the universal fixture positioning apparatus mounted to the universal fixture receiving unit of FIGS. 3 and 4.

As seen in FIG. 5, universal fixture-receiving unit 350 is assembled with mounting unit 320 so that the base plate 352 of the fixture-receiving unit is disposed in the slot 346 of the mounting unit. Thus, the lips at the edges of the base plate are disposed beneath the flanges 342 and 344 of the mounting unit. The lengthwise direction of base plate 352 and, hence, edges 354 and 356 (FIGS. 4A and 4B) extend in the track direction 340 defined by the mounting unit. The cradle axis 392 of the fixture-receiving unit is perpendicular to the track direction 340. The second edge 356 (FIG. 4B) of the base plate on the fixture-receiving unit is disposed beneath flange 342 of the first rail 336 on the mounting unit, whereas the first edge 354 of the fixture-receiving unit (FIG. 4B) is disposed beneath flange 342 of the second rail 338. In the position illustrated in FIG. 5, some of the detent notches 394 (FIG. 4B) on the base plate 352 are engaged with some of the detent bumps 348 (FIG. 3B) on first rail 336. However, the distance between edges 356 and 354 of the fixture-receiving base plate is slightly less than the distance between rails 336 and 338, so that the fixture-receiving unit can be shifted slightly in the direction towards rail 338 and transverse to track direction 340 to disengage the detent bumps and detent notches. In this shifted condition, the fixture-receiving unit 350 is slidable along track or slot 346 in track direction 340 relative to the mounting unit 320.

Stop 349 of the mounting unit is disposed within slot 358 of the base plate. The stop limits the range of travel of the fixture-receiving unit relative to the mounting unit. At one extreme, the first end riser 360 of the fixture-receiving unit is aligned with the end of mounting unit 320 towards the top of the drawing in FIG. 5. At the opposite extreme of the range of motion, the other end riser 362 is aligned with the opposite end of mounting unit 320. Thus, at all positions within the range of motion allowed by stop 349 and slot 358, the fixture-receiving unit 350 is disposed entirely within the length of mounting unit 320 in the track direction 320.

Figure 6:
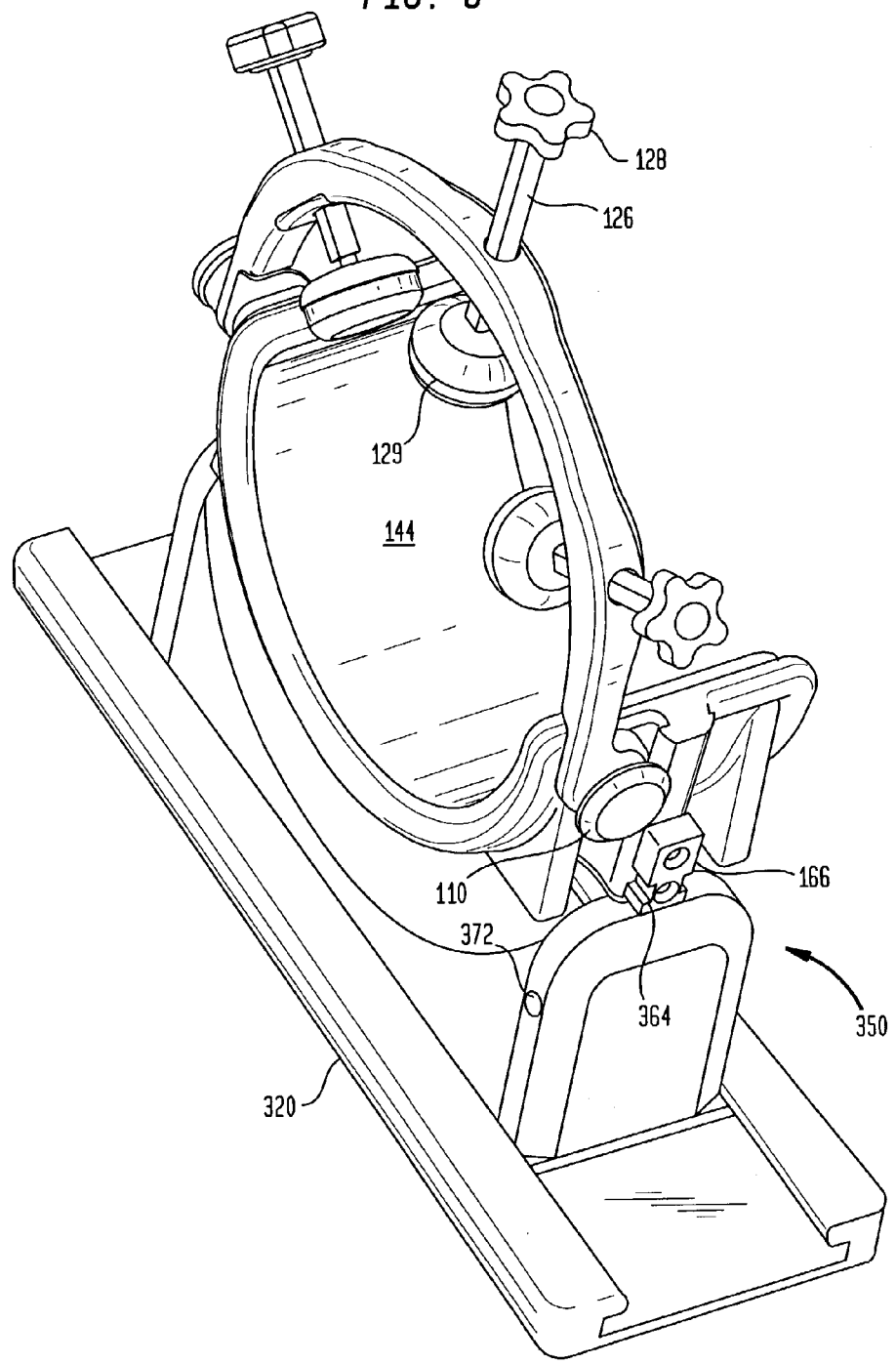
FIG. 6 is a perspective view of the immobilization device mounted to the universal receiving unit, which is mounted to the universal mounting unit.

As shown in FIG. 6, the fixture-positioning assembly of FIGS. 3, 4 and 5 can be used with the head coil device 100 of FIG. 1. The device 100 is engaged with the fixture-receiving unit 350 by positioning the device 100 as shown in FIG. 6 and advancing the device 100 downwardly towards the universal fixture-receiving unit, so that block 166 enters into the slot 364 in end riser 362 and the corresponding block on the opposite side of device 100 enters into the slot 376 (FIG. 5) of end unit 360. As the blocks enter into the slots, they force the catches 366 and 377 (FIGS. 4A and 5) out of the slots against the bias of the spring arms. The catches have sloping surfaces facing towards the open ends of the slots for this purpose. When the coil is fully seated and the blocks are bottomed in the slots of the end units, the latch 366 within slot 364 engages in one of the slots 168 or 170 on block 166, and the corresponding latch 377 of end riser 360 engages the block on the other side in a similar fashion. Thus, the device 100 is firmly held in the end units.

Figure 7:
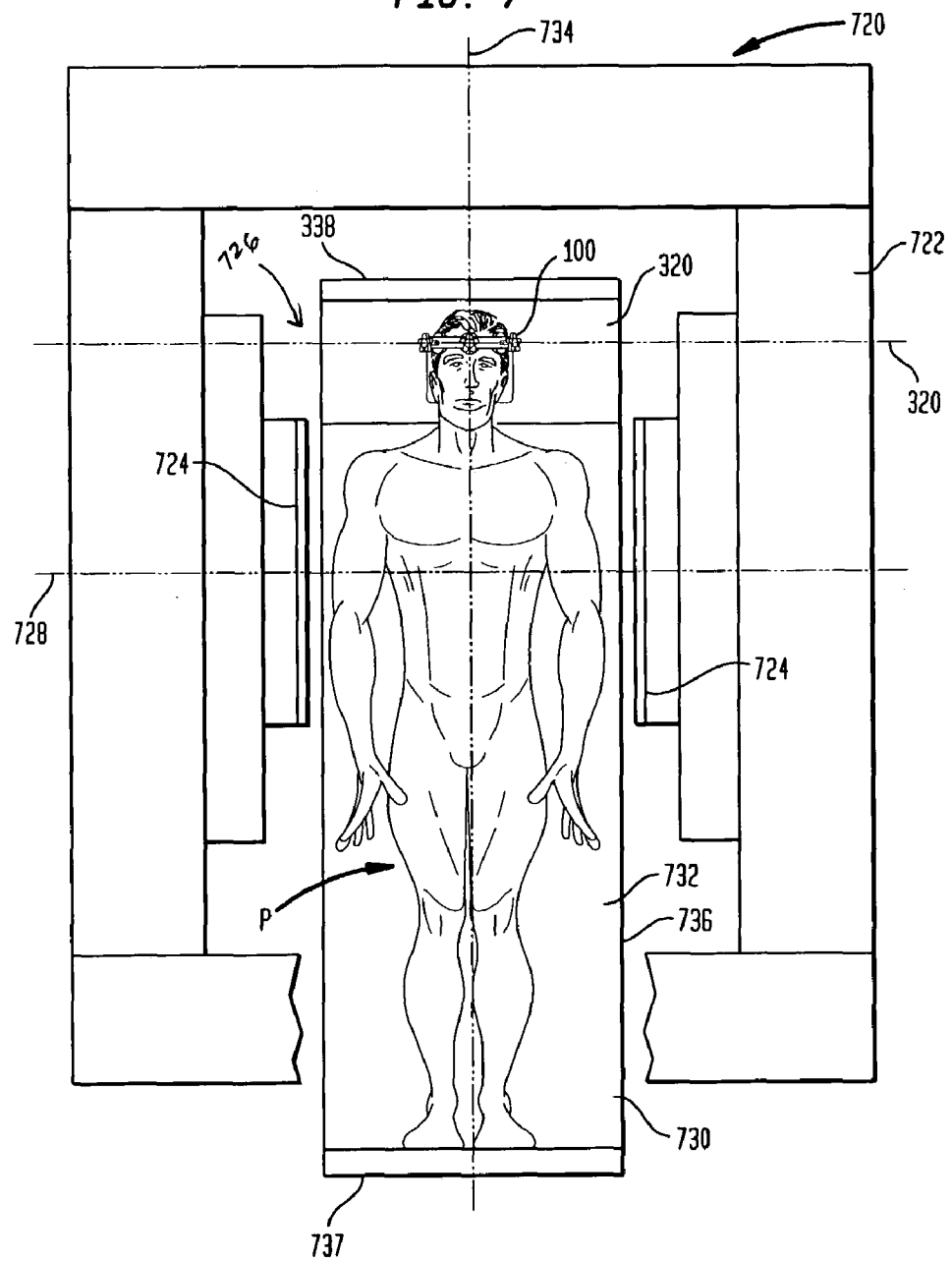
FIG. 7 is a front view of an imaging system in accordance with an aspect of the present invention.
Figure 8:
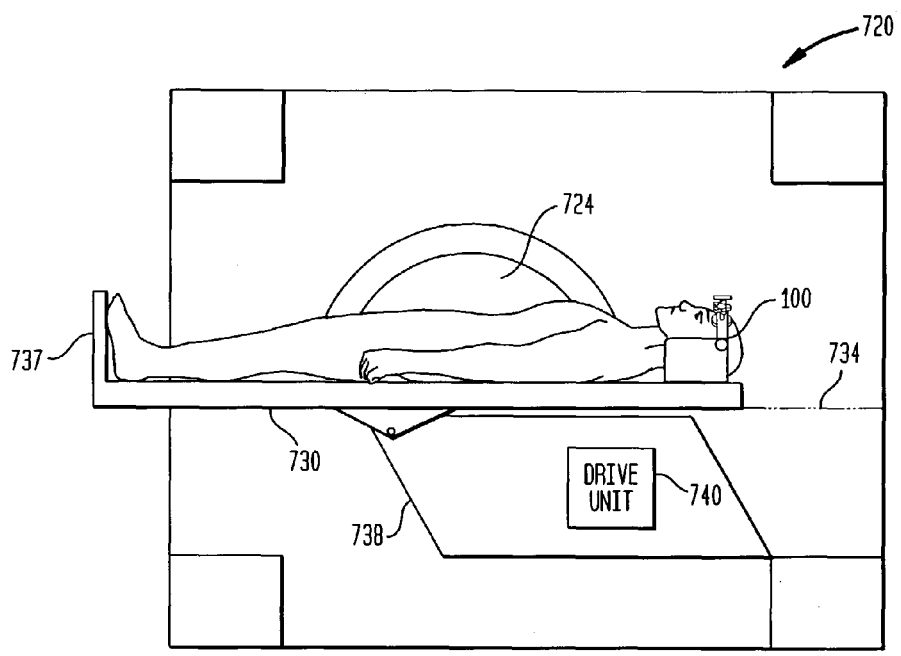
FIG. 8 is a side view of the system of FIG. 7 with a patient in a substantially horizontal position.

The head immobilization device 100 and fixture positioning apparatus is employed in conjunction with a magnetic resonance imaging apparatus 720, as shown in FIG. 7. The particular apparatus illustrated is generally in accordance with the disclosure of the aforementioned '490 patent and the '946 application. It includes a magnet 722 that has a pair of opposed elements 724 defining a patient-receiving gap 726 between them. In the particular magnet illustrated, the opposed elements are pole faces, but in other types of magnets, opposed elements may be elements of superconducting or resistive electromagnet coils or other structures. The magnet is arranged to provide a magnetic field parallel to a magnet axis 728 within patient-receiving gap 726. The magnet axis extends substantially horizontally. The magnetic resonance imaging apparatus further includes a patient handling apparatus incorporating an elongated patient support 730 having a patient-receiving surface 732 and a longitudinal direction 734. A footrest 737 projects from surface 732 at one end. The patient-receiving surface is bounded by a pair of longitudinal edges 736. In the condition illustrated in FIG. 7, the patient-receiving surface lies in a generally vertical plane and the longitudinal direction 734 of the patient support extends generally vertically, typically within about 15 degrees of vertical. The widthwise or lateral dimension of the patient-receiving table transverse to longitudinal direction 734 is just slightly less than the dimension of gap 726 between opposed elements 724 of the magnet. The lateral dimension of the patient support is parallel to magnet axis 728. In FIG. 8 the patient lies in a generally horizontal plane with the longitudinal direction 734 of the patient support extending generally horizontally.

Patient support 730 is associated with a carriage 738 and drive 740 arranged to move the patient support 730 in its direction of elongation and to tilt the support between the horizontal position illustrated and a vertical position (shown in FIG. 7) in which the patient-receiving surface 732 and longitudinal direction 734 are generally vertical.

In accordance with a method aspect of the present invention, the head and neck immobilization device 100 is mounted to the patient-receiving surface 732 with the first member 103 in the flipped-up positioned. The patient is then positioned on the patient-receiving surface 732 such that the back of the patient's head is brought to rest against the surface 144. The first member 103 is then positioned in front of the patient's head such that the contact surface 129 is resting against the patient's forehead. The positioning rods 126 are then tightened so as to immobilize the patient's head and neck. Once immobilized imaging may then proceed, with the patient in variety of positions from substantially upright to horizontal. In addition, the patient may be placed in the sitting position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for head immobilization comprising:
   one or more positioning members;
   a first substantially C-shaped member having an inner surface, an outer surface, first and second fastening apertures and one or more positioning apertures for insertion of said one or more positioning members;
   a second substantially C-shaped member having an inner surface, an outer surface and first and second fastening apertures, said second substantially C-shaped member being secured to said first substantially C-shaped member such that a portion of said outer surface of said first substantially C-shaped member is positioned inside a portion of said inner surface of said second substantially C-shaped member and partially confronts said inner surface of said first substantially C-shaped member; and
   wherein said first and second C-shaped members are secured at each of said first and second apertures to form a halo adapted to accept a human head such that said first or second C-shaped member pivots about an axis which extends through the first and second fastening apertures.

2. The device of claim 1 wherein said first and second C-shaped members are secured by a pivot assembly such that said first C-shaped member pivots towards said second C-shaped member to allow access to the device.

3. The device of claim 1 wherein each of said one or more positioning members further comprise a rod member having a flattened portion that terminates a substantially circular portion.

4. The device of claim 3 wherein each of said one or more positioning apertures further include a flexible magnetically translucent retainer that engages said rod member such that when said rod member circular portion is adjacent said retainer said rod member is held in place and when said rod member flattened portion is adjacent said retainer said rod member is not held in place.

5. The device of claim 4 wherein each of said one or more positioning rods include a first end and a second end and wherein said first end is terminated by a knob that is located outside said first C-shaped member outer surface and said second end is terminated by a patient contact portion that is located inside said first C-shape member inner surface.

6. The device of claim 5 wherein said patient contact portion comprises a circular pad.

7. The device of claim 1 wherein said second C-shaped member further includes a curved base pad that forms said second C-shaped member and defines said second C-shaped member inner and outer surfaces, said base pad having first and second longitudinal edges and arcuate edges that terminate said first and second longitudinal edges so as to define a surface on said pad that is adapted to abut the back of the head when operable.

8. The device of claim 7 further comprising an arcuate rib member formed in said outer surface, said rib member having a pair of mounting connections for attaching the device to a patient support surface associated with a magnet resonance imaging apparatus.

9. System for magnetic resonance imaging comprising:
   a magnet defining a patient-receiving space and having a static magnetic field with a field vector in a substantially horizontal direction;
   a patient support disposed within said patient-receiving space, said patient support having a surface adapted to receive a fixture; and
   a fixture having at least one positioning member, a first substantially C-shaped member and a second substantially C-shaped member, said second substantially C-shaped member having an inner surface, an outer surface and first and second fastening apertures and said first substantially C-shaped member having an inner surface, an outer surface, first and second fastening apertures and at least one positioning aperture for insertion of said at least one positioning member, and
   wherein said first and second C-shaped members are secured to one another by respectively adjacently positioning said first and second fastening apertures of said substantially C-shaped member next to said first and second fastening apertures of said second substantially C-shaped member to form a halo adapted to accept a human head such that said first or second C-shaped member pivots about an axis which extends through the first and second fastening apertures.

10. The system of claim 9 wherein said first C-shaped member and second C-shaped member are connected at their ends such that a portion of said first member outer surface is inside a portion of said second member inner surface at said first and second apertures.

11. The system of claim 9 wherein said first and second C-shaped members are secured by a pivot assembly such that said first and second C-shaped members may be pivoted about each other.

12. The system of claim 9 wherein each of said one or more positioning members further comprise a rod member having a flattened portion that terminates a substantially circular portion.

13. The system of claim 12 wherein each of said one or more positioning apertures further include a flexible magnetically translucent retainer that engages said rod member, such that when said rod member circular portion is adjacent said retainer said rod is held in place and when said rod member flattened portion is adjacent said retainer said rod is not held in place.

14. The system of claim 9 wherein said second C-shaped member further includes an curved base pad that forms said second C-shaped member and defines said first C-shaped member inner and outer surfaces, said base pad having first and second longitudinal edges and arcuate edges that terminate said first and second longitudinal edges so as to define a surface on said pad that is adapted to abut the back of a human head.

15. A method of magnetic resonance imaging comprising:
positioning a patient on a patient support in a space between a pair of opposed pole faces separated apart from one another along a horizontal pole axis such that the head of the patient is located within a head immobilization halo having one or more positioning rods, a first substantially C-shaped member having an inner surface, an outer surface and first and second fastener apertures, a second substantially C-shaped member having an inner surface, an outer surface, first and second fastening apertures and one or more rod apertures for insertions of said one or more positioning rods, and wherein said first and second C-shaped members are secured to one another by respectively adjacently aligning said first and second fastening apertures of said first substantially C-shaped member with said first and second fastening apertures of said second substantially C-shaped member to form a halo adapted to receive a patient's head such that each end of the first C-shaped member pivots about a pivot axis which extends through the first and second fastening apertures;
establishing a substantially horizontal static magnetic field between the pole faces; and
eliciting magnetic resonance signals by transmitting RF energy to the body of the patient and receiving said magnetic resonance signals.

16. The method of claim 15 wherein positioning comprises positioning the patient in substantially upright positioning.

17. The method of claim 15 wherein positioning comprises positioning the patient in a standing position.

18. The method of claim 15 wherein positioning comprises positioning the patient in a sitting position.

19. The method of claim 15 wherein positioning comprises positioning the patient in a substantially horizontal position.

* * * * *